United States Patent
Sun et al.

(10) Patent No.: US 8,420,341 B2
(45) Date of Patent: Apr. 16, 2013

(54) METHODS FOR MEASURING ADP

(75) Inventors: Zhong-Ping Sun, Watchung, NJ (US); Shihong Li, Edison, NJ (US); Conrad Leung, Iselin, NJ (US); Guo-Juan Liao, Edison, NJ (US)

(73) Assignee: Genewiz Inc., Suzhou, Suzhou, Jiangsu (CN)

(*) Notice: Subject to any disclaimer, the term of this patent is extended or adjusted under 35 U.S.C. 154(b) by 286 days.

(21) Appl. No.: 12/682,957

(22) PCT Filed: Nov. 12, 2008

(86) PCT No.: PCT/US2008/083156
§ 371 (c)(1),
(2), (4) Date: Apr. 14, 2010

(87) PCT Pub. No.: WO2009/079120
PCT Pub. Date: Jun. 25, 2009

(65) Prior Publication Data
US 2010/0227344 A1  Sep. 9, 2010

Related U.S. Application Data

(60) Provisional application No. 61/007,676, filed on Dec. 14, 2007.

(51) Int. Cl.
*C12Q 1/48* (2006.01)

(52) U.S. Cl.
USPC .............................................. 435/15

(58) Field of Classification Search .................. 435/15
See application file for complete search history.

(56) References Cited

U.S. PATENT DOCUMENTS

| | | | | | |
|---|---|---|---|---|---|
| 4,019,961 | A | * | 4/1977 | Klose et al. ..................... | 435/15 |
| 4,303,752 | A | * | 12/1981 | Kolehmainen et al. ........... | 435/8 |
| 4,923,796 | A | * | 5/1990 | Deneke et al. .................. | 435/15 |
| 6,068,971 | A | * | 5/2000 | Berry et al. ...................... | 435/4 |
| 6,410,254 | B1 | * | 6/2002 | Finer et al. ...................... | 435/21 |
| 7,410,755 | B2 | | 8/2008 | Charter et al. | |
| 2005/0153381 | A1 | * | 7/2005 | Marusich et al. ............ | 435/7.92 |

\* cited by examiner

*Primary Examiner* — Ralph Gitomer
(74) *Attorney, Agent, or Firm* — Scully, Scott, Murphy & Presser, P.C.

(57) ABSTRACT

This invention relates to assays for detecting and measuring ADP. In particular, this invention provides homogeneous luminescent assays that detect ADP generation and measures ADP accumulation based on enzymatic coupling reactions. The assays of the present invention can be applied to all types of kinases and other ADP-generating enzymes, are antibody free, beads free, radioisotope free, and compatible with commonly used kinase buffers.

2 Claims, 4 Drawing Sheets

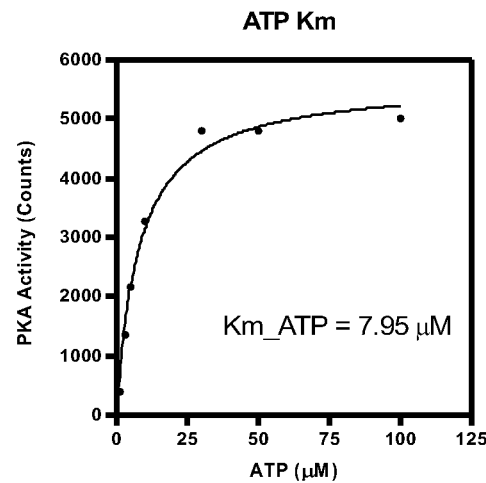
Figure 3
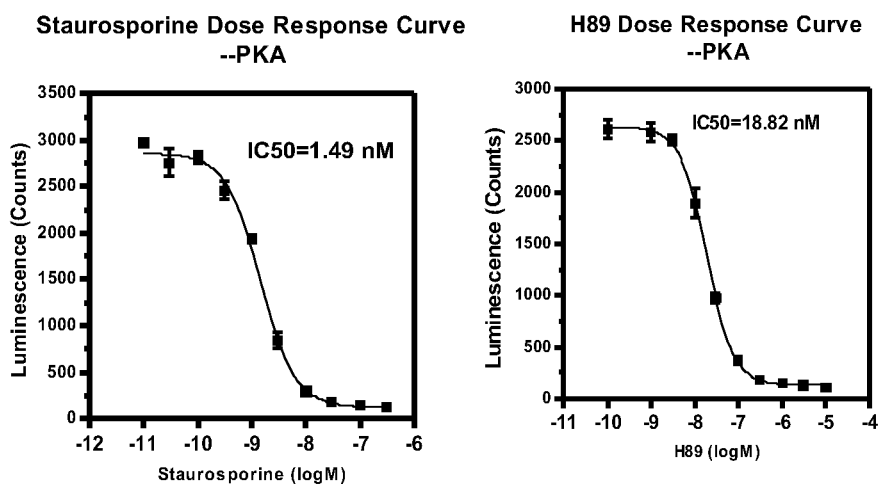
Figure 4A
Figure 4B

METHODS FOR MEASURING ADP

CROSS-REFERENCE TO RELATED APPLICATIONS

This application is a §371 national phase of PCT International Application No. PCT/US2008/083156, filed Nov. 12, 2008, which claims the benefit of U.S. Provisional Application No. 61/007,676 filed on Dec. 14, 2007, the contents of each of which are herein incorporated by reference in its entirety.

FIELD OF THE INVENTION

This invention relates generally to assays for detecting and measuring ADP. In particular, this invention relates to homogeneous luminescent assays that detect ADP generation and measures ADP accumulation based on enzymatic coupling reactions. The assays of the present invention can be applied to all types of kinases and other ADP-generating enzymes, are antibody free, beads free, radioisotope free, and compatible with commonly used kinase buffers.

BACKGROUND OF THE INVENTION

Phosphorylation occurs in majority of signal transduction cascades, and plays pivotal roles in cellular functions such as proliferation, differentiation, metabolism and apoptosis. Kinases, which catalyze phosphorylation of proteins, peptides, lipid and other substrates, have been the focus for both pharmaceutical industry and research laboratories. Since the discovery that many oncogenes encode protein kinases in mid 70s, great efforts have been made to develop kinase regulators that may be useful for treating diseases associated with aberrant kinase functions. The efforts have led to successful development of a number of small molecule kinase regulators. Gleevec, a small molecule inhibitor specific for tyrosine kinase c-abl, was approved by FDA for use in treating chronic myeogeneous leukemia. Irresa and Tarceva, both small molecule inhibitors of EGFR kinase, were approved by FDA in 2003 and 2005, respectively, for use in treating non-small cell lung carcinoma. Bay43, a small molecule inhibitor of raf kinase, was approved by FDA for use in treating kidney cancer. The success has fueled more efforts for the drug discovery industry to search for more kinase inhibitors in order to treat more diseases. These efforts all start with development of appropriate kinase assays amenable for high throughput screening.

The human genome encodes for 518 protein kinases that are responsible for the phosphorylation of 30% of cellular proteins. In addition to protein kinases, lipid kinases and sugar kinases play equally important roles in cellular functions. On one hand, each kinase has a unique substrate, be it a peptide, protein, lipid or carbohydrate. On the other hand, all kinases use ATP and generate ADP.

Besides kinases, there are many other ADP-generating enzymes are or clinical importance. Particularly, an ATPase activity is associated with many different types of proteins, including molecular chaperones, myosin, kinesins, and transporter proteins, many of them are emerging drug targets. Disruption of microtubule function and/or assembly is one approach that is being pursued for development of anticancer agents. A good example of molecular chaperone is HSP90. Being required for proper folding and stability of a number of oncogenic "client" proteins (including c-Raf-1, cdk4, ErbB2, and c-Met), HSP 90 is widely pursued as a target for cancer drug discovery.

Most kinase assays are substrate-specific and are developed to measure the incorporation of phosphate into the unique substrates. The classic kinase assays measure the incorporation of gamma-$P^{33}$ into the substrate. These assays use radioactive isotope, require filtration separation and are low throughput. More recent assays follow the same principle but remove the need for either radioactive isotopes or filtration separation. For example, in some assays, peptide substrates are conjugated with biotin and captured with streptavidin-coated plates. Phosphorylated peptide products are then detected with specific antibodies with colormetric, fluorescent or time-delayed fluorescent readout. In these ELISA type of assays, besides the drawback that washing steps limit throughput, the assays are applied to tyrosine kinases only since, so far, only anti-phosphorylated tyrosine antibodies are available. In SPA assays, streptavidin-coated microbeads impregnated with scintillant are used to capture the biotinylated peptide and measure the incorporation of gamma-$P^{33}$. An improvement over classic kinase assays is that no filtration separation is needed any more; however, these SPA assays still require the use of radioactive materials. ALPHA screen removes the needs for radioactive materials but requires two beads systems and special instruments. In addition to the cost, its sensitivity to light and temperature variations limit its wide implementation. Microfluidic technologies make it possible to separate and measure phosphorylated products on microchips. However, the requirement for special instrument and the relatively low throughput, again, limits its wide implementation.

Other assays measure organic phosphate to assess kinase activity. Some assays utilize chemicals (such as malachite) that change color upon binding of organic phosphate (Innova, Anaspec and Bioassay system). Other assays utilize enzyme coupling reactions to convert phosphate to chromogenic or fluorogenic signals (Invitrogen). However, due to the presence of phosphate in most biological samples, it is difficult to control background and to achieve desirable sensitivity.

The Kinase-Glo™ assay, developed by Promega, is the first universal kinase assay that targets ATP, the substrate shared by all kinases. The assay is universal because it applies to all kinases and other enzymes that use ATP as a substrate. However, because this assay measures the reduction of ATP, the sensitivity of the assay is limited. The ADP-Quest™ assay, from the company DiscoverX, measures the increase of ADP, the product generated by all kinases. However, the incompatibility of the ADP-Quest™ assay with several reagents commonly used in kinase assays, limits its application. In addition, like all homogeneous assays with fluorescent readout, the ADP-Quest™ assay is vulnerable to interference stemming from fluorescent compounds. In comparison with the Kinase-Glo™ assay, this assay has an improved sensitivity.

With the development of monoclonal antibodies that can distinguish ADP from ATP (affinity for ADP is 100 fold stronger than ATP), Bellbrook made a Transcreener™ kinase assay kit available to the industry. In this assay, ADP generated from a kinase reaction competes with labeled tracers for the antibody. Binding of ADP to its antibody results in dissociation of a tracer, and thus reduction of fluorescent signals. One major drawback of this assay is limitation of sensitivity because a signal reduction is being measured. Another drawback of the assay is that it cannot scale up to a 1536 well format.

Therefore, there is a need for improved kinase assays.

SUMMARY OF THE INVENTION

The present invention provides homogeneous luminescent assays that detect ADP generation and measures ADP accumulation based on enzymatic coupling reactions. The assays of the present invention can be applied to all types of kinases and other ADP-generating enzymes, are antibody free, beads free, radioisotope free, and compatible with all commonly used kinase buffers.

According to the present invention, appropriate enzymes and substrates of an enzyme-coupling scheme are provided, which scheme captures ADP produced in a kinase reaction, and generates NADH or NADPH, which then drives the generation of luminescence or fluorescence.

The present invention provides several enzyme-coupling schemes suitable for use in an assay. In one embodiment, the enzyme-coupling scheme utilizes pyruvate kinase and pyruvate dehydrogenase. In another embodiment, the enzymatic scheme utilizes Acetyl-CoA Synthetase and pyruvate dehydrogenase or ketaglutarate dehydrogenase. In still another embodiment, the enzymatic scheme utilizes Succinyl-CoA Synthetase and Ketoglutarate dehydrogenase. In a further embodiment, the enzymatic scheme utilizes Acetyl-CoA Synthetase and CoA-glutathionine reductase. In another embodiment, the scheme utilizes Succinyl-CoA Synthetase and CoA-glutathionine reductase.

Once NADH or NADPH is generated from ADP and the enzyme coupling reactions, NADH or NADPH will drive the generation of luminescence when provided with appropriate compounds (such as FMN) and enzymes (such as FMN: NADH Oxidoreductase and luciferase); or fluorescence if provided with Resazurin and diaphorase.

The present invention further provides kits containing reagents for practicing the assays of the present invention.

BRIEF DESCRIPTION OF THE DRAWINGS

FIG. 1A: ADP titration up to 50 µM. FIG. 1B: ADP titration up to 5 µM.

FIG. 3 shows the plot for measurement of ATP Km.

FIGS. 4A-4B show the plots for measuring IC50 of PKA inhibitors, Staurospotine (FIG. 4A) and H89 (FIG. 4B).

DETAILED DESCRIPTION OF THE INVENTION

Figure 1A:
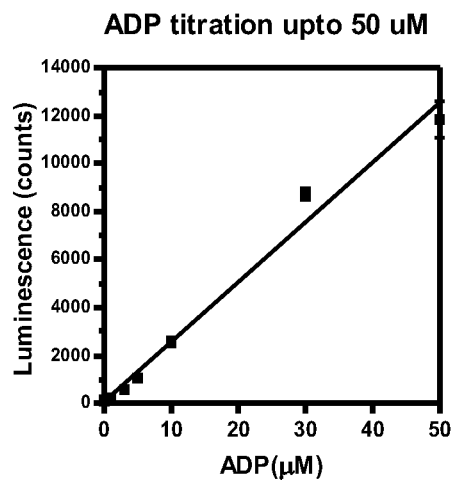
FIGS. 1A-1B demonstrate that luminescence generated in an assay of the present invention correlates with the amount of ADP.

The present inventors have developed assays that measure ADP through one or more enzyme coupling reactions that lead to the production of NADH or NADPH, which, in turn, drives the generation of luminescence or alternatively, fluorescence.

One advantage of the assays provided by the present invention is that the present assays are universal. By "universal" is meant that the assays of the present invention can be used to assess the presence and/or activity of any kinases or to screen for inhibitors of any kinases, including but not limited to Tyrosine protein kinases, Serine/Threonine protein kinases, lipid kinases and carbohydrate kinases. By "universal" is also meant that the assay of the present invention can be applied to any other proteins or enzymes that generate ADP such as an ATPase. An ATPase activity is associated with many different types of proteins, including molecular chaperones, myosin, kinesins, and transporter proteins, many of them are emerging drug targets. The present assays are also scalable and are compatible with all commonly used kinase buffers and reagents. In addition, the present assays, especially assays that generate luminescence, are much more sensitive than assays such as the ADP-Quest™ assay. The improved sensitivity makes the present assays useful for assessing both strong and weak kinases. Furthermore, the luminescent readout of the present assays makes it less vulnerable to compound interference.

In the presence of the kinase, ADP will be produced given an appropriate substrate and ATP:

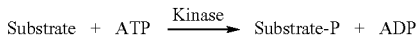

The general principle of the assays of the present invention is to provide appropriate enzymes and substrates of an enzyme-coupling scheme, which scheme captures ADP, and generates NADH or NADPH, which then drives the generation of luminescence.

According to the present invention, several enzyme-coupling schemes can be used in an assay. In one embodiment, the enzyme-coupling scheme utilizes pyruvate kinase and pyruvate dehydrogenase. In this scheme shown below, ADP is amplified and drives the conversion of phosphoenolpyruvate to pyruvate. Pyruvate then transfers its proton to NAD and converts it to NADH.

1.

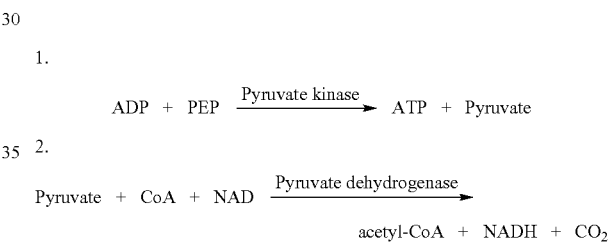

In another embodiment, the enzyme-coupling scheme amplifies ADP and drives the generation of CoA. CoA is then amplified and drives the generation of NADH, or alternatively NADPH. In one specific embodiment, the scheme utilizes Acetyl-CoA Synthetase (*G. lamblia*) and pyruvate dehydrogenase or ketoglutarate dehydrogenase.

1.

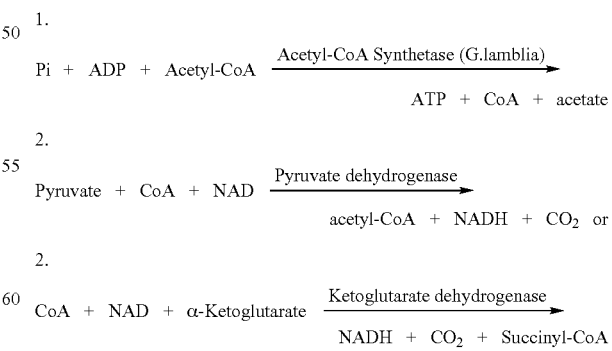

In another specific embodiment, the scheme utilizes Succinyl-CoA Synthetase and Ketoglutarate dehydrogenase or pyruvate dehydrogenase.

1.

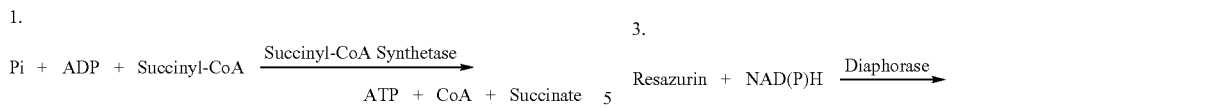

2.

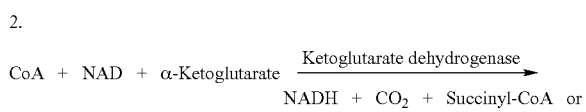

2.

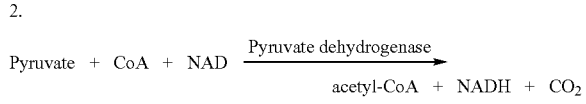

In still another specific embodiment, CoA is generated by using either Acetyl-CoA Synthetase or Succinyl-CoA Synthetase, which then drives the generation of NADPH as follows:

2.

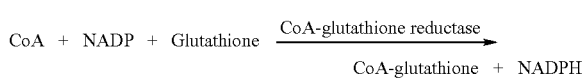

Once NADH or NADPH is generated and provided with appropriate compounds (such as riboflavin monophosphate and long chain aldehyde) and enzymes (such as FMN: NADH Oxidoreductase and luciferase), NADH or NADPH will drive the generation of luminescence.

3.

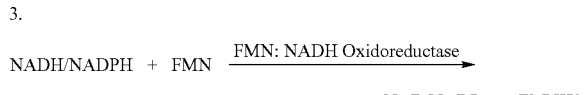

4.

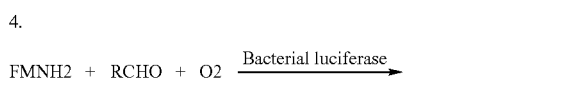

Alternatively, compounds and enzymes can be provided so that NADH or NADPH drives the generation of fluorescent signals. For example:

3.

Resorufin could be excited at 535 nm and the excited resorufin emits at 590 nm.

In still another embodiment, the present invention contemplates creating an ADP-specific Luciferase by making a site-directed mutation(s) in a wild type ATP-dependent luciferase. Once such ADP-dependent Luciferase is generated, ADP can be measured directly in one step.

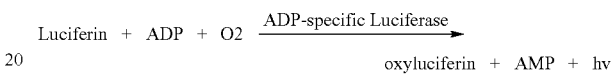

Enzymes useful for practicing the assays of the present invention can be obtained from various species, by conventional purification or by recombinant production. Alternatively, enzymes can be obtained from various commercial sources.

TABLE 1

| Enzyme | Examples of Natural Sources | Examples of Commercial Sources or GenBank Accession No. |
|---|---|---|
| Pyruvate kinase | Rabbit, bovine or porcine liver, muscle, brain, and the like | Roche, Sigma, USB |
| Pyruvate dehydrogenase | Bovine or porcine heart muscle | Sigma |
| Acetyl-CoA Synthetase | G. lamblia | AF107206 |
| Succinyl-CoA Synthetase | microorganism or mammalian tissues | |
| Ketoglutarate dehydrogenase | Bovine or porcine heart muscle | Sigma |
| CoA-glutathione reductase | microorganism | |
| FMN: NADH Oxidoreductase | photobacteria | Roche |
| Bacterial luciferase | photobacteria | Roche, Sigma |
| Diaphorase | microorganism | Sigma, Roche |

According to the present invention, the assays are typically carried out in microtiter well plates in small volumes ranging from about 5 to 500 μl, more usually from about 10 to 100 μl. The temperature for the assay is generally in the range of about 10 to 40° C., or conveniently at room temperature. The time for the assay may depend upon a specific enzymatic reaction. For example, when the ADP is produced by an enzyme reaction, the time for the reaction is at least about 5 minutes, and usually is about 10-60 minutes.

The order of addition of the components may vary depending upon whether some of the components have been pre-combined for simultaneous addition and whether the assay is an endpoint assay or a kinetic assay. In certain specific embodiments, a first reagent is added to a sample containing ADP (e.g., a kinase reaction mixture), wherein the first reagent contains necessary components of selected enzyme coupling reactions, including the enzymes and substrates, and the mixture is allowed to be incubated at an appropriate temperature for a time sufficient to permit the enzyme coupling reactions to substantially complete, resulting in the production of NAD(P)H. Subsequently, a second reagent is added to the reaction mixture, wherein the second reagent contains components necessary for developing luminescence or fluorescence, and a reading may be taken immediately or shortly thereafter.

The amounts of the various reagents (including the enzymes) in the assay mixture may vary depending on the enzyme coupling reactions chosen. The following tables provide some general guidance for the concentrations of various components in an assay mixture in accordance with the present invention. Components other than those specifically listed in the tables may also be present.

TABLE 2

| Component | General Range | Preferred Range |
| --- | --- | --- |
| Pyruvate kinase | 0.1-500 mU/ml | 0.2-200 mU/ml |
| Pyruvate dehydrogenase | 0.1-500 mU/ml | 0.2-200 mU/ml |
| PEP | 2-2000 μm | 10-500 μM |
| CoA | 2-2000 μM | 10-500 μM |
| NAD | 2-2000 μM | 10-500 μM |
| TPP | 2-2000 μM | 10-500 μM |
| buffer | 1-200 mM | 10-100 mM |
| MgCl2 | 0.1-50 mM | 0.2-20 mM |

TABLE 3A

| Component | General Range | Preferred Range |
| --- | --- | --- |
| Acetyl-CoA Synthetase | 0.1-2000 mU/ml | 0.2-500 mU/ml |
| Pyruvate dehydrogenase | 0.1-500 mU/ml | 0.2-200 mU/ml |
| Acetyl-CoA | 1-2000 μM | 2-200 μM |
| Potassium Phosphate | 1-200 mM | 10-100 mM |
| Pyruvate | 2-2000 μM | 1-200 μM |
| NAD | 2-2000 μM | 10-500 μM |
| buffer | 1-200 mM | 10-100 mM |
| MgCl2 | 0.1-50 mM | 0.2-20 mM |
| TPP | 2-2000 μM | 10-500 μM |

TABLE 3B

| Component | General Range | Preferred Range |
| --- | --- | --- |
| Acetyl-CoA Synthetase | 0.1-2000 mU/ml | 0.2-500 mU/ml |
| ketoglutarate dehydrogenase | 0.1-1000 mU/ml | 0.2-200 mU/ml |
| Acetyl-CoA | 1-2000 μM | 2-200 μM |
| Potassium Phosphate | 1-200 mM | 10-100 mM |
| Alpha-ketoglutarate | 2-8000 μM | 5-500 μM |
| NAD | 2-2000 μM | 10-500 μM |
| buffer | 1-200 mM | 10-100 mM |
| MgCl2 | 0.1-50 mM | 0.2-20 mM |
| TPP | 2-2000 μM | 10-500 μM |

TABLE 4

| Component | General Range | Preferred Range |
| --- | --- | --- |
| Succinyl-CoA Synthetase | 0.1-2000 mU/ml | 0.2-500 mU/ml |
| Ketoglutarate dehydrogenase | 0.1-1000 mU/ml | 0.2-200 mU/ml |
| Succinyl-CoA | 1-2000 μM | 2-200 μM |
| Potassium Phosphate | 1-200 mM | 10-100 mM |
| α-Ketoglutarate | 2-8000 μM | 5-500 μM |
| NAD | 2-2000 μM | 10-500 μM |
| TPP | 2-2000 μM | 10-500 μM |
| MgCl2 | 0.1-50 mM | 0.2-30 mM |
| buffer | 1-200 mM | 10-100 mM |

TABLE 5

| Component | General Range | Preferred Range |
| --- | --- | --- |
| Acetyl-CoA Synthetase | 0.1-2000 mU/ml | 0.2-500 mU/ml |
| CoA-glutathionine reductase | 0.1-2000 mU/ml | 0.2-500 mU/ml |
| Acetyl-CoA | 1-2000 μM | 2-200 μM |
| Potassium Phosphate | 1-200 mM | 10-100 mM |
| Glutathione | 2-2000 μM | 10-500 μM |
| NADP | 0.2-2000 μM | 1-100 μM |
| buffer | 1-200 mM | 10-100 mM |

TABLE 6

| Component | General Range | Preferred Range |
| --- | --- | --- |
| Succinyl-CoA Synthetase | 0.1-2000 mU/ml | 0.2-500 mU/ml |
| CoA-glutathionine reductase | 0.1-2000 mU/ml | 0.2-500 mU/ml |
| Succinyl-CoA | 1-2000 μM | 2-200 μM |
| Glutathione | 2-2000 μM | 10-500 μM |
| NADP | 0.2-2000 μM | 1-100 μM |
| buffer | 1-200 mM | 10-100 mM |

TABLE 7

| Component | General Range | Preferred Range |
| --- | --- | --- |
| FMN: NADH Oxidoreductase | 0.5-1000 mU/ml | 1-300 mU/ml |
| FMN | 0.05-500 μM | 0.1-100 μM |
| Bacterial luciferase | 0.002-5 mg/ml | 0.002-1 mg/ml |
| RCHO (Decanal or Dodacanal) | 0.0001-0.05% | 0.0005-0.01% |
| Enzyme stablizer | 1-50% | 2-40% |
| buffer | 1-200 mM | 10-100 mM |

TABLE 8

| Component | General Range | Preferred Range |
| --- | --- | --- |
| Diaphorase | 0.5-1000 mU/ml | 1-200 mU/ml |
| Resazurin | 0.01-1000 μM | 0.1-100 μM |
| Enzyme stablizer | 1-50% | 2-40% |
| buffer | 1-200 mM | 10-100 mM |

Various conventional buffers can be employed in conjunction with the reagents suitable for use in selected enzyme coupling reactions. The buffers include phosphate, Hepes, Tris, MOPS, among others. A particular buffer may be chosen in accordance with the nature of the system producing the ADP. The pH of the buffer is generally about 7, but can be varied from 6-9. Other conventional additives may also be included in a buffer, such as, for example, nonionic detergent, BSA, DTT, DMSO, among others. The present invention also provides kits containing various reagents for determining ADP. The various reagents can be provided in individual containers.

The following examples are provided to describe the invention in further detail. These examples are intended to illustrate specific applications of the methods of the invention and should in no way be construed as limiting the invention.

Example 1

Reagents

All of the substrates, buffers, enzymes and cofactors for steps 1 and 2 of an enzyme-coupling scheme, described above, can be supplied in a single mixture, Reagent A. All of the substrates, buffers, enzymes and cofactors for step 3 and 4 can be supplied in Reagent B. Reagents A and B having the following compositions were used in the assays described here in below.

| Compositions | |
|---|---|
| Reagent A | Reagent B |
| Hepes | Hepes |
| DTT | DTT |
| MgCl2 | beta-glycerol phosphate |
| | NaF |
| phosphoenolpyruvate | Glycerol |
| coenzyme A | Non-ionic detergent |
| thiamine pyrophosphate | riboflavin momophosphate |
| Nicotinomide adenine dinucleotide | decyl aldehyde or other long chain aldehyde |
| Pyruvate Kinase | EDTA |
| Pyruvate dehydrogenase | luciferase (containing NADH: FMN oxidoreductase) |

Assay Procedures
1. Add 10 µl reagent A to 30 µl kinase reaction mixtures and incubate at RT.
2. Add 10 µl reagent B and read luminescence immediately.

Example 2

Luminescence Correlates with Amount of ADP

Figure 1B:
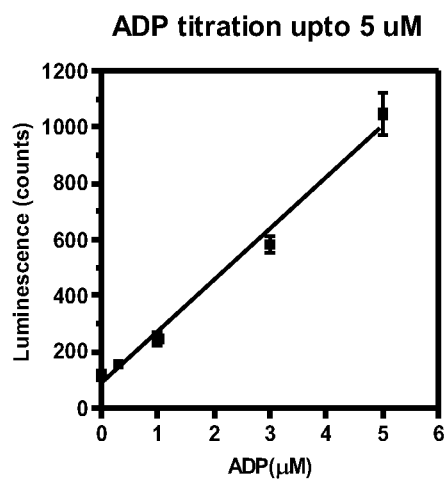

30 µl of 0, 0.3, 1, 3, 5, 10, 30 and 50 µM of ADP in kinase buffer (20 mM Hepes, pH7.5, 10 mM MgCl2 and 1 mM DTT) were aliquoted in a solid white 96 well plate, and 10 µl of reagent A were added to each well. The plate was incubated at room temperature for 15 minutes. At the end of incubation, 10 µl of Reagent B were added to each well and luminescence was measured immediately using a DTX880 multimode detector. The results, summarized in Table 2, were plotted as shown in FIGS. 1A-1B. Each data point is the average of 12 repeats.

TABLE 2

| ADP(µM) | z' | s/n |
|---|---|---|
| 1 | 0.80 | 2.1 |
| 3 | 0.76 | 5.0 |
| 5 | 0.77 | 8.9 |
| 10 | 0.79 | 21.9 |
| 30 | 0.92 | 74.0 |
| 50 | 0.80 | 100.5 |

"z'" measures the reproducibility of the assay. Z' = 1 − 3 * (stdev of signal + stdev of background)/(signal-background). For a good assay, z' has to be bigger than 0.5. The bigger the Z', the better the assay.
"s/n" represents signal to noise ratio.

As the plots show, a direct relationship exists between luminescence measured with ADP Lumina and the amount of ADP. The assay is sensitive and reproducible. For example, 1 µM and 5 µM ADP produced 2.1 fold and 8.9 fold signal over noise, respectively, with the value of Z' at or close to 0.8. When coupled to kinase reactions, ADP was recycled and the signal was amplified, and thus, the sensitivity was increased further.

Example 3

Luminesence Correlates with Kinase Activity and Reaction Time

Figure 2:
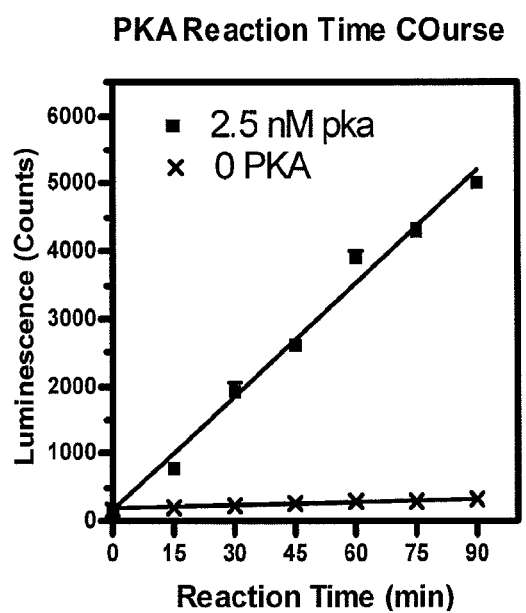
FIG. 2 demonstrates that luminescence generated in an assay of the present invention correlates with kinase activity and reaction time.

30 µl PKA reactions in 20 mM Hepes, pH7.5, 10 mM MgCl2 and 1 mM DTT, with 5 µM ATP, 30 µM Kemptide, 0 or 2.5 nM PKA were incubated with 10 µl Reagent A at room temperature for 0, 15, 30, 45, 60, 75 and 90 minutes. At the end of incubation, 10 µl Reagent B were added and luminescence measured. The results are shown in FIG. 2. Each data point represents the average of 3 repeats. As shown in FIG. 2, a direct linear correlation exists between luminescence and PKA reaction time. When no PKA is added, no ADP is generated and hence, no luminescence increases.

Example 4

ATP Km Measured

30 µl PKA reactions in 20 mM Hepes, pH7.5, 10 mM MgCl2 and 1 mM DTT, with 30 µM Kemptide, 2.5 nM PKA and increasing amounts of ATP were incubated with 10 µl Reagent A at room temperature for 20 minutes. At the end of incubation, 10 µl Reagent B were added and luminescence was measured. The results are shown in FIG. 3. Each data point represents the average of 3 repeats. As shown FIG. 3, ATP km is consistent with those reported in the literature.

Example 5

IC50 of Two PKA Inhibitors Measured

30 µl PKA reactions in 20 mM Hepes, pH7.5, 10 mM MgCl2 and 1 mM DTT, with 5 µM ATP, 30 µM Kemptide, 2.5 nM PKA and increasing amounts of staurosporine or H89 were incubated with 10 µl Reagent A at room temperature for 90 minutes. At the end of incubation, 10 µl Reagent B were added and luminescence was measured. The results are shown in FIGS. 4A-4B. Each data point represents the average of 3 repeats. As shown FIGS. 4A-4B, the kinase inhibitors decreased luminescence signals in a dose dependent manner, and their IC50 are consistent with those reported in the literature.

Example 6

IC50 of a PI3 Kinase Inhibitor Measured

Figure 5:
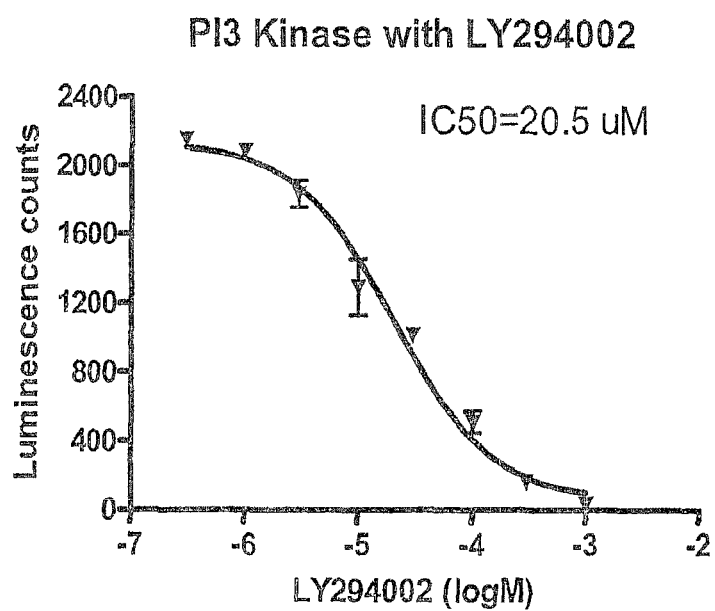
FIG. 5 shows the plot for measuring IC50 of a PI3 kinase inhibitor.

Increasing amounts of Ly294002 were incubated with 2 ng/ul of PI3 kinase as described above for 90 minutes at room temperature. Reagent A was added at the end of reaction and incubation was continued for 15 more minutes. Then Reagent B was added and luminescence was measured. The results are shown in FIG. 5. Each data point represents the average of 3 repeats. As shown FIG. 5, luminescence signal decreased with increasing doses of the inhibitor.

REFERENCES

Kostich, M., English, J. et al., Genome Biol, 2002, 3:RESEARCH0043;
Manning, G., Whyte, D. B. et al., Science, 2002, 298:1912-34;
Cohen, P., Trends Biochem Sci, 2000, 25:596-601;
Sridhar, R., Hanson-Painton, O. et al., Pharm Res, 2000, 17:1345-53;

Cohen, P., Nat Rev Drug Discov, 2002, 1:309-15
Hanks, s. Genome Biol, 2003, 4:111
Dancey, J. and Sausville, E. A., Nat Rev Drug Discov, 2003, 2:296-313
Ross, H., Armstrong, C. G. et al., Biochem J, 2002, 366:977-81
Sills, M. A. et al., J Biomol Screen, 2002, 7:191-214
Wesche, H, Xiao, S-H and Young, S, Combinatorial Chemistry & High Throughput Screening, 2005, 8:181-195
Pellegrini, F. et al., Cancer Invest, 2005, 23:264-73
DeBonis, S. et al., Mol Cancer Ther, 2004, 3:1079-90
Workman, P., Curr Cancer Drug Targets, 2003, 3:297-300
Rowlands, M. G. et al., Anal Biochem, 2004, 327:176-83
Irving, M. G and Williams, J. F, Biochem. J, 1973, 131:287-301
Srivastava, L K and Baquer, N Z, Arch. Biochem. Biophys. 1985, 236(2): 703-713
Stanley, C J and Perham, R N., Biochem J, 1980, 191:147-154
Hasting, J. W., et al, J Biol Chem. 1965, 240(3): 1473-1481

What is claimed is:

1. A method of determining ADP, comprising:
  a) to a sample suspected of comprising ADP, adding a first reagent comprising components of an enzyme coupling scheme for producing NADH or NADPH, to produce an assay mixture;
  b) incubating said assay mixture for sufficient time for the reactions of said enzyme coupling scheme to occur to produce said NADH or NADPH;
  c) adding to said assay mixture a second reagent to drive the generation of light emission, said second reagent comprising:
    (i) FMN:NADH oxidoreductase, FMN, luciferase and RCHO or
    (ii) diaphorase and Resazurin;
  d) determining light emission generated from step c) as a measure of the amount of ADP in said sample.

2. The method according to claim 1, wherein said first reagent comprises components selected from the group consisting of:
  (1) pyruvate kinase, pyruvate dehydrogenase, PEP and NAD;
  (2) Acetyl-CoA Synthetase, pyruvate dehydrogenase or ketoglutarate dehydrogenase, phosphate, acetyl-CoA, pyruvate or a-ketoglutarate, and NAD;
  (3) Succinyl-CoA Synthetase, Ketoglutarate dehydrogenase or pyruvate dehydrogenase, phosphate, succinyl-CoA, a-ketoglutarate or pyruvate, and NAD;
  (4) Acetyl-CoA Synthetase, CoA-glutathionine reductase, phosphate, acetyl-CoA, glutathione and NADP; and
  (5) Succinyl-CoA Synthetase, CoA-glutathionine reductase, phosphate, succinyl-CoA, glutathione and NADP.

* * * * *